(12) United States Patent
Soper et al.

(10) Patent No.: US 8,758,974 B2
(45) Date of Patent: Jun. 24, 2014

(54) PHOTORESIST-FREE MICROPATTERNING ON POLYMER SURFACES

(75) Inventors: Steven A. Soper, Baton Rouge, LA (US); Robin L. McCarley, Prairieville, LA (US); Bikas Vaidya, College Station, TX (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 1484 days.

(21) Appl. No.: 10/734,816

(22) Filed: Dec. 12, 2003

(65) Prior Publication Data
US 2004/0191703 A1 Sep. 30, 2004

Related U.S. Application Data

(60) Provisional application No. 60/458,319, filed on Mar. 27, 2003.

(51) Int. Cl.
*G03F 7/004* (2006.01)
*G03F 7/038* (2006.01)
*G03F 7/20* (2006.01)

(52) U.S. Cl.
USPC ........ 430/270.1; 430/311; 430/319; 430/320; 430/321; 430/322; 430/324; 430/905; 430/910

(58) Field of Classification Search
None
See application file for complete search history.

(56) References Cited

U.S. PATENT DOCUMENTS

| | | | |
|---|---|---|---|
| 3,658,672 A * | 4/1972 | Norris | 205/83 |
| 3,767,579 A * | 10/1973 | Tsubouchi et al. | 252/62.9 PZ |
| 4,945,028 A * | 7/1990 | Ogawa | 430/296 |
| 5,051,312 A | 9/1991 | Allmer | 428/458 |
| 5,229,172 A * | 7/1993 | Cahalan et al. | 427/536 |
| 5,593,814 A * | 1/1997 | Matsuda et al. | 430/320 |
| 5,948,484 A * | 9/1999 | Gudimenko et al. | 427/489 |
| 6,436,615 B1 | 8/2002 | Brandow et al. | 430/324 |
| 6,800,331 B2 * | 10/2004 | Bilyk et al. | 427/387 |
| 7,749,429 B2 * | 7/2010 | Furuzono et al. | 419/23 |
| 7,965,438 B2 * | 6/2011 | Kawahara et al. | 359/296 |
| 2003/0143411 A1* | 7/2003 | Nakagawa | 428/458 |
| 2004/0069649 A1* | 4/2004 | Katayama et al. | 205/125 |
| 2007/0275080 A1* | 11/2007 | Laulicht et al. | 424/493 |

FOREIGN PATENT DOCUMENTS

| | | |
|---|---|---|
| WO | WO 00/56808 | 9/2000 |
| WO | WO 02/18288 | 3/2002 |

OTHER PUBLICATIONS

M. Adams et al., "Surface modification of bisphenol-A-polycarbonate by far-UV radiation. Part I: In vacuum," Polymer Degradation and Stability, vol. 41, pp. 265-273 (1993).

M. Adams et al., "Surface modification of bisphenol-A-polycarbonate by far-UV radiation. Part II: In air," Polymer Degradation and Stability, vol. 42, pp. 145-151 (1993).

(Continued)

*Primary Examiner* — Sin J. Lee
(74) *Attorney, Agent, or Firm* — John H. Runnels

(57) ABSTRACT

A method is described for the direct photochemical modification and micro-patterning of polymer surfaces, without the need to use a photoresist. For example, micropatterns of various functional chemical groups, biomolecules, and metal films have been deposited on poly(carbonate) and poly(methyl methacrylate) surfaces. These patterns may be used, for example, in integrated electronics, capture elements, or sensing elements in micro-fluidic channels.

31 Claims, 11 Drawing Sheets

(56) References Cited

OTHER PUBLICATIONS

A. Henry et al., "Selective deposition of metals on plastics used in the construction of microanalytical devices: Photo-directed formation of metal features on PMMA," *J. Phys. Chem. B*, vol. 105, pp. 8755-8761 (2001).

A. Henry et al., "Surface modification of poly(methyl methacrylate) used in the fabrication of microanalytical devices," *Anal. Chem.*, vol. 72, pp. 5331-5337 (2000).

A. Hozumi et al., Spatially defined surface modification of poly(methyl methacrylate) using 172 nm vacuum ultraviolet light. *Langmuir*, vol. 18, pp. 9022-9027 (2002).

T. Johnson et al., "Chemical mapping of hot-embossed and UV-laser-ablated microchannels in poly(methyl methacrylate) using carboxylate specific fluorescent probes," *Appl. Surf. Sci:*, vol. 181, pp. 149-159 (2001).

Johnson, T. et al., "Laser modification of preformed polymer microchannels: Application to reduce band broadening around turns subject to electrokinetic flow," *Anal. Chem.*, vol. 73, pp. 3656-3661 (2001).

Kamińska, A. et al, "Photosensitized degradation of poly(methyl methacrylate) and polystyrene," *Polish J. Chem.*, vol. 69, pp. 865-872 (1995).

Kavc, T. et al., "Surface modification of polyethylene by photochemical introduction of sulfonic acid groups," *Chem. Mater.*, vol. 12, pp. 1053-1059 (2000).

Liu, Y. et al., "Microfabricated polycarbonate CE devices for DNA analysis," *Anal. Chem.*, vol. 73, pp. 4196-4201 (2001).

Meyer, U. et al., "Surface modification of polystyrene by photoinitiated introduction of cyano groups," *Macromol. Rapid Commun.*, vol. 20, pp. 515-520 (1999).

Schilling, M. et al., "Selective electroless nickel deposition on patterned phosphonate and carboxylate polymer films," *J. Electrochem. Soc.*, vol. 143, pp. 691-695 (1996).

Srinivasan, R. et al., *Polymer*, vol. 26, pp. 1297-1300 (1985).

Vaidya, B. et al., "Micro-patterning and metal deposition on polymer surfaces," abstract, 223rd ACS National Meeting (Apr. 7-11, 2002).

Vaidya, B. et al., "Photoresist-free micropatterning of polymer surfaces used in microanalytical devices," presentation, Micro Total Analysis Systems (Nov. 2002).

Xu, Y. et al., "Solid-Phase Reversible Immobilization in Microfludic Chips for the Purification of Dye-Labeled DNA Sequencing Fragments," *Anal. Chem.*, vol. 75, pp. 2975-2984 (2003).

van der Wel, H. et al., "Surface modification of polycarbonate by u.v. light as studied by TOF-SIMS," *Polymer*, vol. 34, pp. 2065-2071 (1993).

Zhang, J. et al., "Modification of polymers with UV excimer radiation from lasers and lamps," *J. Adhes. Sci. Tech.*, vol. 8, pp. 1179-1210 (1994).

Zhang, J. et al., "Modification of polymers with UV excimer radiation from lasers and lamps," *J. Adhesion Sci.*, vol. 8, pp. 1179-1210 (1994).

\* cited by examiner

PHOTORESIST-FREE MICROPATTERNING ON POLYMER SURFACES

The development of this invention was partially funded by the Government under grants number 1R24 CA84625-01 and 1R01 HG01499-01 awarded by the National Institutes of Health. The Government has certain rights in this invention.

The benefit of the Mar. 27, 2003 filing date of provisional application Ser. No. 60/458,319 is claimed under 35 U.S.C. §119(e).

This invention pertains to imparting chemical functionality on a polymer surface in accordance with a selected pattern, without the use of a photoresist.

Photolithography is one of the most popular techniques for creating micropatterns and microstructures on substrates for various applications. Conventional photolithography requires the use of a photoresist. Most photoresists require the use of organic solvents at various stages, which makes them unsuitable for use on common polymers such as poly(carbonate), PC; and poly(methyl methacrylate), PMMA.

Ultraviolet light has been used to alter polymer surfaces. For example, T. Johnson et al., "Laser modification of preformed polymer microchannels: Application to reduce band broadening around turns subject to electrokinetic flow," *Anal. Chem.*, vol. 73, pp. 3656-3661 (2001) described the modification of PMMA surfaces with a pulsed UV excimer laser (KrF, 248 nm) to reduce band broadening and to increase electroosmotic mobility in embossed microchannels by modifying PMMA surface charges.

R. Srinivasan et al., *Polymer*, vol. 26, pp. 1297-1300 (1985) discloses that exposing polymer surfaces such as PMMA, polyethyleneterephthalate (PET), and polyimide (PI) to far ultraviolet irradiation in air resulted in both photooxidative etching and oxidation to produce groups such as hydroperoxy, peracid, carboxylic, and hydroxy groups.

A. Hozumi et al., "Spatially defined surface modification of poly(methyl methacrylate) using 172 nm vacuum ultraviolet light, *Langmuir*, vol. 18, pp. 9022-9027 (2002) discloses photoetching a PMMA surface using 172 nm ultraviolet light. The hydrophilicity and photooxidation rate both depended on the concentration of oxygen during the UV exposure. XPS spectra suggested that oxygen-containing functional groups were introduced, such as C—O, C=O, and O=C—O. Exposing the surface through a mask at the same wavelength, microgrooves were fabricated on PMMA surfaces. Because the surface wettability of the exposed areas was different from that of the unexposed areas, the authors said that microstructured PMMA substrates might be fabricated with chemically reactive and inert regions on the micrometer scale.

T. Johnson et al., "Chemical mapping of hot-embossed and UV-laser-ablated microchannels in poly(methyl methacrylate) using carboxylate specific fluorescent probes," *Appl. Surf. Sci.*, vol. 181, pp. 149-159 (2001) discloses the formation of microchannels in PMMA through hot embossing or ablation with a 248 nm KrF laser. Carboxylate groups on the surface were fluorescently labeled with an ethyl-dimethylaminopropyl-carbodiimide hydrochloride/amino-fluorescein solution. The results suggested that the surface charges were localized on the corners of the trapezoidal channels formed by the hot imprint method; while charges were distributed more uniformly in the laser ablated microchannels. Laser ablation under nitrogen was found to produce more surface charge than laser ablation under oxygen.

J. Zhang et al., "Modification of polymers with UV excimer radiation from lasers and lamps," *J. Adhes. Sci. Tech.*, vol. 8, pp. 1179-1210 (1994) discloses UV photochemical dry etching and surface modification of polymers including PMMA, polyimide, PET, and polytetrafluoroethylene (PTFE), and discusses the mechanism of photooxidation of PMMA. At page 1189 is a suggestion that the disclosed process afforded control of the micro-roughness of the polymer surface, and that such micro-roughness could be used to promote adhesion of metals to the surface.

Surface modification of polycarbonate by far-UV has been studied in vacuum, in Ar, and in air. M. Adams et al., "Surface modification of bisphenol-A-polycarbonate by far-UV radiation. Part I: In vacuum," *Polymer Degradation and Stability*, vol. 41, pp. 265-273 (1993) reported that in vacuum, far-UV radiation was totally absorbed in the first 100 nm of solid bisphenol-A-polycarbonate (PC), resulting in rapid deoxygenation of the surface and photoablation. On increasing exposure, a cross-linked protective "skin" was formed, inhibiting further deoxygenation and photoablation. Main-chain scission reactions were reported to dominate the degradation mechanism. By contrast, at mid-UV and visible wavelengths, photo-Fries rearrangements were said to be favored. The formation of a cross-linked skin was said to be relevant to photolithographic applications, as it provided a route to selective protection of areas from solvent etching.

M. Adams et al., "Surface modification of bisphenol-A-polycarbonate by far-UV radiation. Part II: In air," *Polymer Degradation and Stability*, vol. 42, pp. 145-151 (1993) reported that in air, far-UV radiation caused a PC surface to be rapidly oxygenated, causing considerable loss of mass, loss of thickness, loss of carbonate functionality, loss of phenylene functionality, and the production of carbonyl-containing functionalities. The dominant photo-reactions were said to be chain scissions, rather than the photo-Fries rearrangement, and the major volatile product was benzoic acid. After several hours of irradiation, quantum yields decreased due to shielding by a layer of involatile oxidation products. By contrast to the vacuum-irradiated case, the surface layer was not cross-linked, but suffered considerable photo-ablation, which was said to provide a possible route for photolithography.

H. van der Wel et al., "Surface modification of polycarbonate by u.v. light as studied by TOF-SIMS," *Polymer*, vol. 34, pp. 2065-2071 (1993) discloses that exposing polycarbonates to UV light (185 and 254 nm) in an argon atmosphere caused main chain scissions and photooxidation. Hydroxyl groups were introduced on the polycarbonate surface, and there was evidence for Photo-Fries rearrangement. It was reported from other studies that, in the presence of oxygen, the photo-products are easily oxidized. It was speculated that the hydroxyl groups on the polymer surface might be used to improve adhesion of a metal layer.

A. Henry et al., "Surface modification of poly(methyl methacrylate) used in the fabrication of microanalytical devices," *Anal. Chem.*, vol. 72, pp. 5331-5337 (2000) describe the chemical modification of PMMA surfaces by an aminolysis reaction with the monoanion of $\alpha,\omega$-diaminoalkanes to yield amine-terminated PMMA surfaces. The amino groups could be reacted with a variety of different compounds to place different functionalities on the surface of PMMA. It was reported, for example, that enzymes could be immobilized on the amine-terminated PMMA surfaces, and that the enzymes retained their activity in the restriction digestion of dsDNAs.

A. Henry et al., "Selective deposition of metals on plastics used in the construction of microanalytical devices: Photo-directed formation of metal features on PMMA," *J. Phys. Chem. B*, vol. 105, pp. 8755-8761 (2001) reports the use of amine-terminated PMMA surfaces as a substrate for the electroless deposition of gold nanoparticle films, the adsorptive deposition of gold colloids, the laterally patterned formation of gold nanoparticle films on PMMA, and the use of the patterned gold films to electrolessly deposit silver films with micrometer features. The patterning was accomplished by the photoremoval of photolabile protecting groups attached to amine functionalities on the PMMA surface, followed by deposition of gold and silver.

A. Kamińska et al, "Photosensitized degradation of poly (methyl methacrylate) and polystyrene," *Polish J. Chem.*, vol. 69, pp. 865-872 (1995), in the context of a discussion concerning the recycling of polymeric waste, discloses that $FeCl_3$ accelerated photooxidative degradation of PMMA; and that thermal stability decreased in UV-preoxidized PMMA.

Y. Liu et al., "Microfabricated polycarbonate CE devices for DNA analysis," *Anal. Chem.*, vol. 73, pp. 4196-4201 (2001) discloses capillary electrophoresis devices fabricated in PC by compression molding, in which aqueous fluid transport was enhanced by UV irradiation treatment of the PC surfaces to increase their hydrophilicity. It was suggested that the increase in hydrophilicity resulted from the formation of carboxylic and carbonylic groups on the PC surface.

U.S. Pat. No. 6,436,615 discloses a process for modifying a substrate (e.g., a polymer substrate) in areas that are exposed to actinic radiation, having the steps: (a) providing on the substrate functional groups adapted for conversion to oxygen-containing photoproducts upon exposure to actinic radiation; (b) exposing at least a portion of the substrate to the actinic radiation, converting the functional groups in an exposed region of the substrate to the photoproducts; (c) contacting the photoproducts with a primary or secondary amine in the presence of hydrogen ions, forming imine groups; and (d) contacting the imine groups with a reducing agent, forming amine groups on the substrate in the exposed region. This patent also discloses a process for modifying a substrate in areas that are unexposed to actinic radiation, having the steps: (a) providing on the substrate aryl functional groups adapted for conversion to oxygen-containing photoproducts upon exposure to actinic radiation; (b) exposing a portion of the substrate to the actinic radiation, converting the aryl functional groups in an exposed region of the substrate to the photoproducts, and not converting the aryl functional groups in an unexposed region of the substrate to the photoproducts; (c) contacting the aryl functional groups in the unexposed region of the substrate with a compound adapted for physisorption to the aryl functional groups, preferentially physisorbing the compound onto the substrate in the unexposed regions. Working examples included coating polymer films containing chloromethylphenyl functionality on silica or silicon wafers, grafting molecules containing amine ligand sites to UV photopatterned films, and metallization at the amine sites.

M. Schilling et al., "Selective electroless nickel deposition on patterned phosphonate and carboxylate polymer films," *J. Electrochem. Soc.*, vol. 143, pp. 691-695 (1996) discloses electroless metallization processes for depositing metallic nickel on photopatterned films of poly(diisopropyl vinylbenzylphosphonate-co-N-methylmaleimide). Spin-coated thin films of certain carboxylic acid polymers were also used as substrates for electroless nickel deposition.

J. Zhang et al., "Modification of polymers with UV excimer radiation from lasers and lamps," *J. Adhesion Sci.*, vol. 8, pp. 1179-1210 (1994) discloses studies conducted in photochemical dry etching and surface modification of PMMA, PI, PET and PTFE with coherent and incoherent excimer UV sources. Ablation rates, decomposition rates, and etch rates of PMMA and PI were determined at different intensities, exposure times, and wavelengths. The etching of PMMA was explained as being the result of extensive photo-oxidation. Electrolessly deposited metal layers were adhered onto the surfaces of some of these polymers. It was noted that the presence of oxygen strongly influences photochemical processes of PMMA.

U.S. Pat. No. 5,051,312 discloses a process for modifying polymer surfaces by contacting the surface with an organic modifying agent while irradiating the surface with UV or visible light that can be absorbed by the modifier.

Published international patent application WO 00/56808 discloses a method for rendering a surface covered by a polymer more hydrophilic by treatment in a gas plasma of a non-polymerizable gas.

Published international patent application WO 02/18288 discloses a method for obtaining microarrays by oxidizing olefinic groups on the surface of a solid support to allow the formation of aldehyde functionalities on the surface, and covalently binding other molecules to the aldehyde functionalities for the detection, identification, quantification, or recovery of a complementary target molecule.

There is an unfilled need for a method to activate polymeric surfaces so that various chemical moieties may be attached to the surfaces in a controlled pattern on a microscale. It has previously been difficult to activate the surfaces of polymers used in microfluidic devices, and to attach functional moieties. Previous solution phase or gas phase techniques have generally suffered from poor adhesion of the substances thereby attached to the polymer surface.

Metallization of polymer surfaces in a controlled micropattern has been particularly difficult to achieve.

We have discovered a photoresist-free method for using actinic light to create, on the surface of a polymer, micropatterns characterized by the presence of functional groups, covalently attached biomolecules, metals, or other moieties. The micro-pattern begins with the generation of attached carboxyl groups on the polymer surface, to which other compounds may then be reacted or conjugated.

Exposing suitable polymers to broadband or narrow-band actinic light in an oxidative atmosphere activates the polymer surface, promoting photooxidation, and generating carboxyl groups where the actinic light was directed, carboxyl groups that remain bound to the polymer. The technique may be used on the surfaces of many polymers that absorb ultraviolet light, e.g., acrylate polymers (e.g., PMMA); aromatic polymers (e.g., polystyrene, phenoxy resins); polyimides; and polysulfones. Copolymers may also be used.

Polysulfones may be particularly useful. They typically undergo fewer side reactions, and tend to have high glass transition temperatures. Polysulfones, as well as phenoxy resins, are generally more hydrolytically stable than are polycarbonates, especially under conditions of strong acid or strong base.

The atmosphere in which the exposure occurs should be oxidative. In many applications, ordinary air is suitable, although it would also be possible to use an atmosphere with a higher or lower concentration of oxygen (or other oxidizing agent) to modify the patterning if desired. Higher concentrations of oxygen would be expected to facilitate surface oxidation. Other oxidizing agents known in the art may be used in lieu of, or in addition to, oxygen, for example $SO_2$, $NO_2$, or CNBr. See, e.g., T. Kavc et al., "Surface modification of polyethylene by photochemical introduction of sulfonic acid groups," *Chem. Mater.*, vol. 12, pp. 1053-1059 (2000); U. Meyer et al, "Surface modification of polystyrene by photoinitiated introduction of cyano groups," *Macromol. Rapid Commun.*, vol. 20, pp. 515-520 (1999).

In a nitrogen (or other inert) atmosphere, a polycarbonate will undergo reactions such as the following in response to UV light:

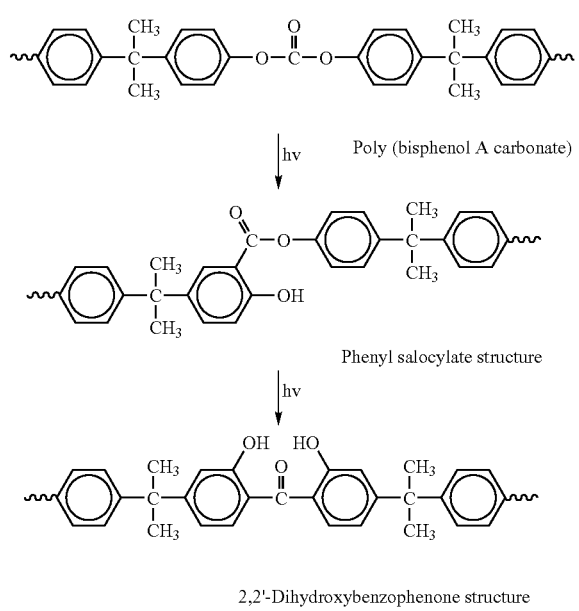

By contrast, without wishing to be bound by this theory, it is believed that in an oxidative atmosphere reactions such as the following can occur in PC:

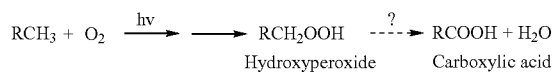

Bound, carboxyl-terminated functionalities on the PMMA surface result in an oxidative atmosphere. Without wishing to be bound by this theory, the carboxyl groups are most likely formed by cleavage of the methyl ester, but there may also be some oxidation of the methyl groups attached to the polymer backbone:

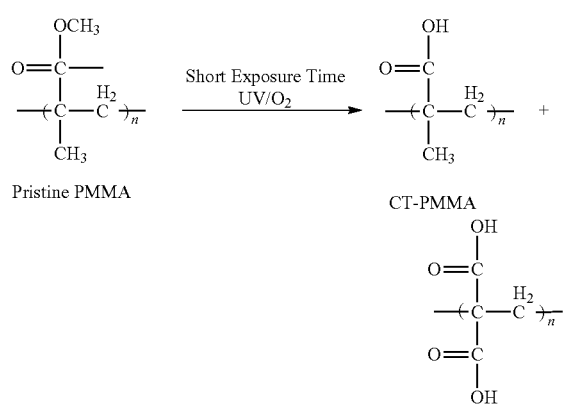

The photooxidation of polymers is, of course, a known phenomenon. But photooxidation of polymers has generally been considered a problem to avoid, not an opportunity to exploit, as is done in the present invention. For example, in "traditional" processes for making microdevices using PMMA as an X-ray resist, it has been the usual practice to eliminate oxidative conditions, by, e.g., exposure in a nitrogen or helium atmosphere, or in a vacuum.

We have found that the invention works well with broadband ultraviolet light, although it will also work with narrow band UV lamps (e.g., 254 nm) or even UV lasers at frequencies absorbed by the polymers being used. The "active sites" may be selectively patterned by exposure through a photomask, or by direct "writing" on the surface with a focused UV source, or by other means for selectively exposing portions of the surface to actinic light, while leaving the remaining portions of the surface substantially unexposed to actinic light.

The ability to reliably pattern a polymeric surface opens the door to many possibilities. Even if no further modifications follow the photooxidation step, the oxidative products (e.g., carboxyl groups) alter the hydrophobicity of the polymer surface, making it easier to wet, and changing the electroosmotic flow properties. Thus the photooxidation alone can provide direct benefits.

The patterned carboxyl groups on the surface also provide functionality to which other chemical groups may be selectively attached. For example, solid phase reversible immobilization (SPRI) allows one to selectively bind and then to release such entities as dsDNA, plasmids, PCR reaction products, and many others. The invention thus, for example, provides a vehicle to isolate and purify nucleic acids.

Functionality may be introduced by reacting the surface carboxyl groups with any of a variety of reactants. Examples of reactants that may be used to impart functionality include, for example, the following: oligonucleotides, antibodies, antigen-binding portions of antibodies, antigens, enzymes, non-enzymatic peptides, non-enzymatic proteins, a reduced or oxidized metal such as copper, nickel, gold, silver, platinum, or palladium, metal oxides, ceramics, piezoelectric materials, semiconductors, amines, imides, azides, azo compounds, cyanates, alcohols, thiols, anhydrides, thionyl halides, and other polymers. To introduce a second polymer functionality, one might use a pre-formed polymer directly as the reactant, or one might employ as a reactant a polymer initiator or a monomer, and then form a second polymer in situ by reaction of monomer with the bound initiator or bound monomer. Another option is to bind one or more whole, respiring cells to chemical functionality on the polymer substrate.

Depending on the nature of the reactant used to impart additional functionality, the carboxyl groups that are initially bound to the polymer substrate may remain in carboxyl form, be converted to carbonyl form, or be replaced with another group altogether. E.g., alcohols are converted to bound esters, amines are converted to bound amides, thiols are converted to bound thiol esters, thionyl halides are converted to carboxylic acid halides, etc.

If the chemical functionality has at least one nitrogen, sulfur, or oxygen atom with a lone pair of electrons, that lone pair may coordinate to reduced or oxidized metal atoms. After coordinating an oxidized metal atom to a nitrogen, sulfur, or oxygen atom's lone pair, the coordinated metal atom may optionally be reduced in situ. The reduced metal remains selectively bound to the patterned portions of the polymer surface through coordination to the lone pair of electrons on the nitrogens, sulfurs, or oxygens.

The present invention minimizes detrimental side reactions such as loss of mass, loss of thickness, and photoablation by controlling process parameters such as wavelength (a wavelength of about 254 nm being preferred for many applications), exposure intensity, and exposure time. Preferably, the fluence of actinic light on the exposed portions of the polymer surface suffices to generate at least about $10^{-12}$ moles per cm$^2$ of carboxyl groups that remain bound to the polymer; and the fluence in the exposed portions is insufficient to cause photoablation of polymer deeper than about 250 nm; while the fluence of light in the unexposed portions of the surface is zero, or is sufficient to induce the generation of not more than about $5 \times 10^{-13}$ moles per cm$^2$ of carboxyl groups that remain bound to the polymer.

DNA, antibody, or antigen microarrays on polymeric surfaces may be prepared through the use of this invention. Previously, such microarrays have generally been prepared on glass or silica substrates.

Preferred polymers that have been used in prototype experiments are poly(methyl methacrylate) ("PMMA") and polycarbonate ("PC"). Polysulfones are also expected to be promising.

Figure 1:
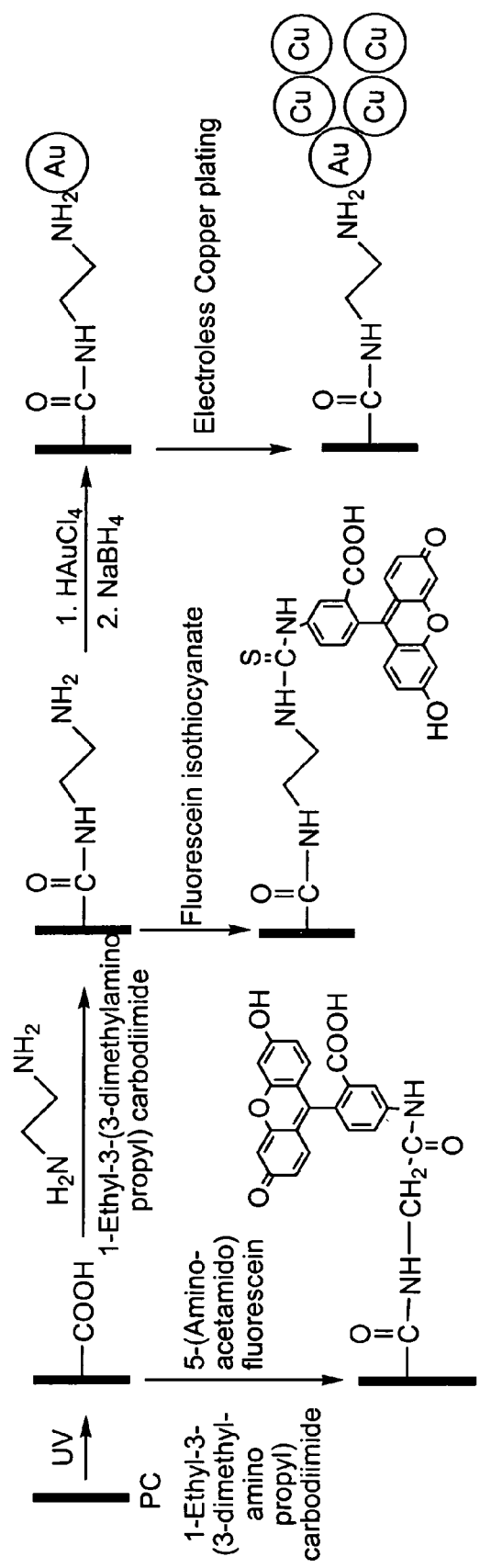
FIG. 1 depicts the chemistry of one reaction scheme to micropattern a polymer surface with UV light, and then to plate it with metal.

Examples using the invention are described below.
Experimental (General)

Poly(carbonate) sheets (PC), either Lexan™ (General Electric) or Makrolon™ (Bayer), and poly(methyl methacrylate) sheets (PMMA), Plexiglass™ or Lucite™, were purchased from commercial sources and were machined into various-sized pieces. HPLC grade isopropanol and other chemicals were obtained from Aldrich, and were used without further purification. PMMA and PC surfaces were cleaned with isopropanol and dried under N$_2$, and were then exposed to UV light through a photo mask.

Sessile drop contact angle values on polymer surfaces were measured with a VCA 2000 contact angle system equipped with a CCD camera (VCA, Billerica, Mass.), using the software provided by the manufacturer. Approximately 2 μL of deionized (18 MΩ·cm) water was placed on the polymer surface with a syringe, and the contact angle of the water droplet was measured immediately thereafter. The measurements were repeated at least five times on each substrate, and the average was reported with an error of one standard deviation.

Fluorescent dyes were covalently attached to the UV-modified (carboxylated) polymer surface either directly or after conversion of the surface carboxyl groups to amines by coupling with ethylene diamine in aqueous solution with a coupling agent, 1-ethyl-3-(3-dimethyl-aminopropyl)carbodiimide, EDC.

In a general scheme for the formation of metal films on polymer surfaces, UV-induced oxidation first forms a layer on the surface of the polymer, a layer containing functional groups (e.g., carboxyl, thiol, or amino) to which metal ions will bind. Next, the layer is exposed to a solution containing metal ions, and the metal ions bind to the functional groups. A reducing agent reduces the adhering metal ions to a reduced metal particle layer. Amine functionality or other nitrogen-containing functionality may, for example, coordinate to reduced metals through the lone pair of electrons on the nitrogen atom. A further metal film may then be deposited, for example, via electroplating, or with an electroless bath (containing metal ions and a reducing agent), or both. For example, the initial metal deposited might be a thin gold layer, to which copper may then be deposited by electroplating or electroless deposition. For example:

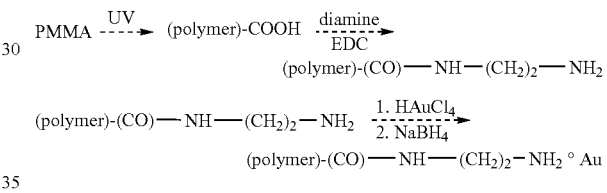

To deposit metal, the surface carboxylate groups were first converted to amine groups by reaction with diamine and EDC. A gold seed layer was then deposited on the aminated surface by treating the surface with AuCl$_4^-$ solution, followed by sodium borohydride reduction of the AuCl$_4^-$ coordinated to the amine groups, using the method of A. Henry et al., *J. Phys. Chem. B*, vol. 105, pp. 8755-8761 (2001). Metal films were formed on the gold seed layer with an electroless metal plating bath (0.9 M formaldehyde, 0.02 M cupric sulfate, 0.1 M potassium sodium tartrate, pH adjusted to ~11 with KOH), using the method of P. Moberg et al., *Electrochem. Soc.*, vol. 144, pp. L151-L153 (1997).

Metal films may also be formed by electroplating. Metal films that may be deposited on the gold seed layer include, for example copper, silver, gold, and nickel. Micrometer metal features may be used, for example, as microcircuitry, microelectrodes, microfluidic devices, and as microheaters. Microheaters may be useful, for example, in micro-polymerase chain reaction chips.

FIG. 1 depicts the chemistry of one reaction scheme to micropattern a polymer surface with UV light, and then to plate it with metal.

EXAMPLES 1 AND 2

UV irradiation of PC and PMMA surfaces in the presence of oxygen chemically modified the surfaces, making them more hydrophilic. Water contact angles for 2 μL water droplets, measured on unmodified and UV-treated PC, were 84° and 50°, respectively. The water contact angle of 70° for a pristine PMMA surface changed to 40° after UV exposure.

EXAMPLES 3-5

Figure 2A:
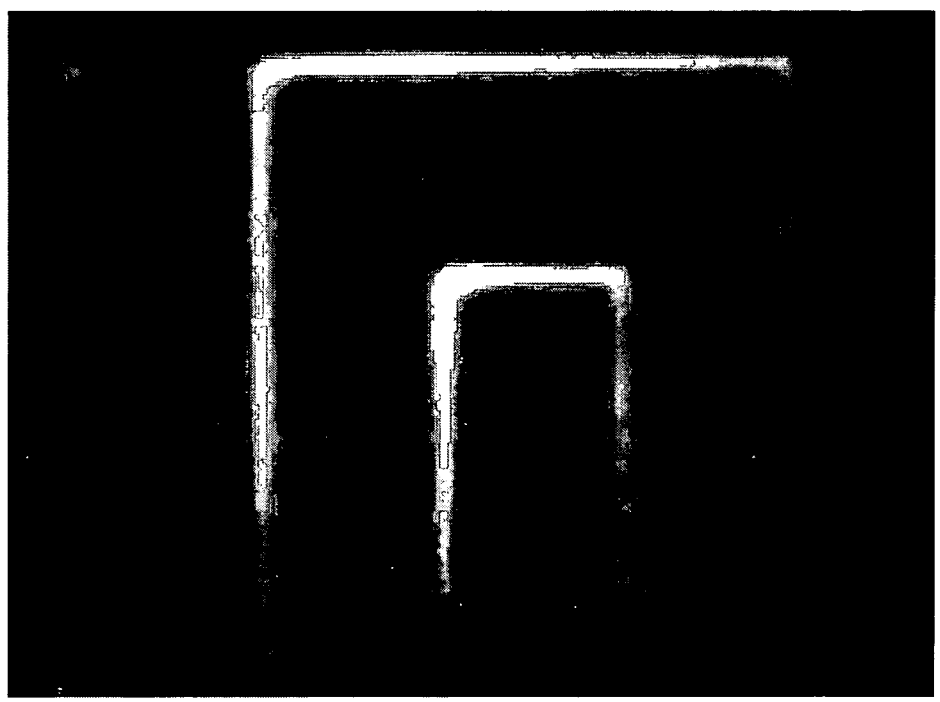
FIG. 2(a) depicts a photomicrograph of 10 μm fluorescent lines patterned on PC using the leftmost reaction scheme of FIG. 1.
Figure 2B:
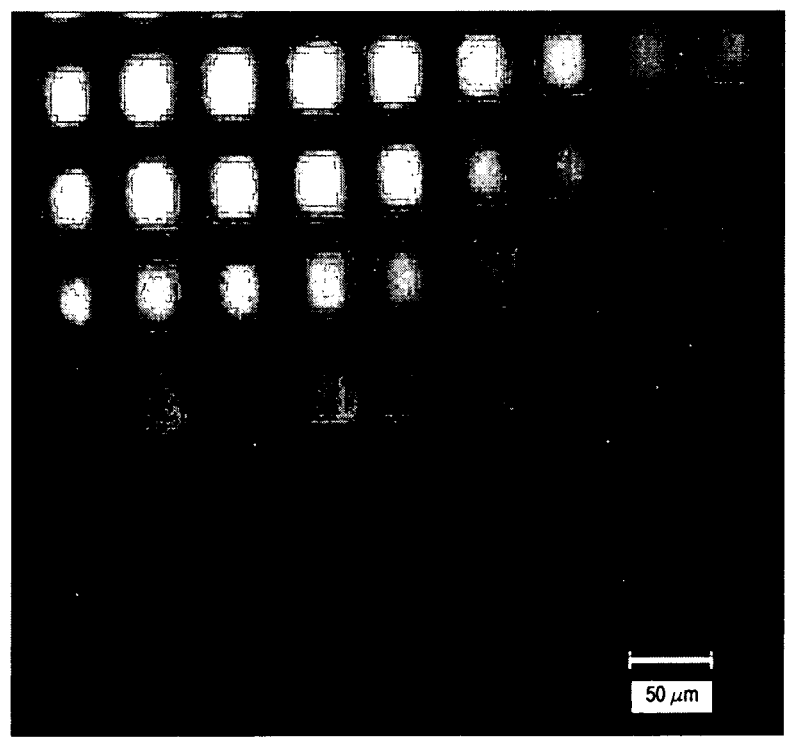
FIG. 2(b) depicts a photomicrograph of 50 μm fluorescent squares patterned on PMMA using the center reaction scheme of FIG. 1.
Figure 3:
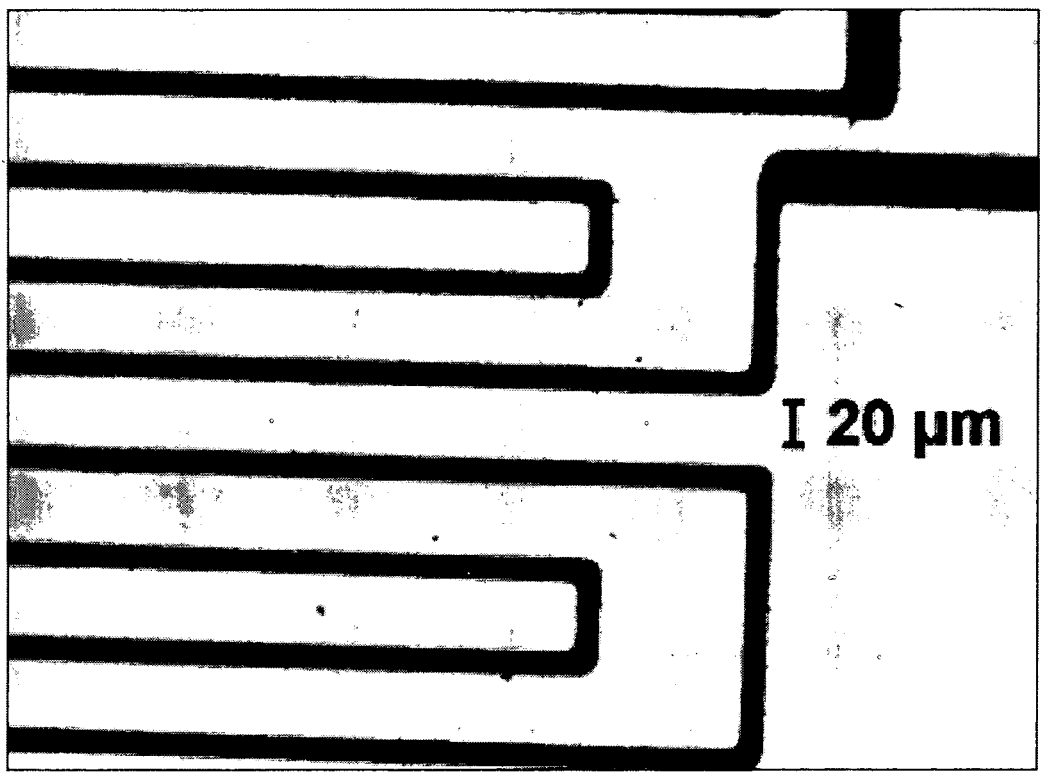
FIG. 3 depicts a photomicrograph of copper microelectrodes patterned on PC using the rightmost reaction scheme of FIG. 1.

FIG. 2(a) depicts a photomicrograph of 10 μm fluorescent lines patterned on PC using the leftmost reaction scheme of FIG. 1. FIG. 2(b) depicts a photomicrograph of 50 μm fluorescent squares patterned on PMMA using the center reaction scheme of FIG. 1. FIG. 3 depicts a photomicrograph of copper microelectrodes patterned on PC using the rightmost reaction scheme of FIG. 1.

As shown in FIG. 2(a), after UV irradiation of a PC surface, followed by treatment with 5-(aminoacetamido)fluorescein and EDC, fluorescence was observed only in the area that had been exposed to UV light. As shown in FIG. 2(b), after UV irradiation of a PMMA surface, followed by treatment with a diamine and EDC, fluorescence was observed only in the area that had been exposed to UV light. Copper microelectrodes have also been deposited on both PC and PMMA surfaces, with an example on a PC surface shown in FIG. 3. These results confirmed that the photo-induced oxidation of both PC and PMMA generated carboxylate groups on the surfaces.

This direct method of surface modification provides a means to covalently attach micro-domains of various enzymes, antibodies, proteins, etc. on polymer surfaces. The ability to deposit microstructures of metals on plastic surfaces makes the novel technique particularly useful in the fabrication of microcircuits and micro-electrodes in micro-fluidic devices.

FURTHER EXAMPLES

Solid-Phase Reversible Immobilization for the Purification of DNA on PC-Photoactivated Surfaces One method for purifying cycle sequencing reaction products before electrophoretic sorting is solid-phase reversible immobilization (SPRI). At high concentrations of polyethylene glycol (PEG) and salt, DNAs bind to the surface of carboxyl-coated magnetic particles. Once bound, the DNA-bead complexes are washed, and are then eluted in water to yield purified DNA. A good binding buffer for magnetic bead purification of DNA fragments for capillary gel electrophoresis sequencing has been reported to be a solution of 5% tetraethylene glycol (TEG) and 57.4% ethanol.

Agencourt sells a magnetic bead-based dye-terminator purification kit, CleanSEQ™, based on this technique. Magnetic beads are coated with a carboxylate layer, and then DNA is suspended in a solution containing TEG, which permits selective precipitation and immobilization of the DNA onto the magnetic beads. After the target DNA is immobilized, a magnetic field is applied and the beads are washed with ethanol to remove salts, excess dye-labeled terminators, and other soluble components. Then the DNA is released from the magnetic support by rinsing with water.

By contrast to other solid phase methods, SPRI does not require a streptavidin-coated solid support, nor biotinylated primers or probes attached to particles. Because excess biotinylated primers compete for a limited number of streptavidin sites on beads, one must exercise caution in these solid phase methods by removing unextended primers. This step may contribute to lower yield and poorer quality of the resulting DNA. The DNA elution step in SPRI is very simple, while the DNA fragments obtained using biotin/streptavidin are typically eluted by heating in an EDTA/formamide mixture.

The SPRI technique is conducive to automation, can be scaled to small volumes to reduce the quantity of reagents needed for sequencing reactions, and may readily be adapted for microfluidic devices.

We have purified cycle sequencing reaction products using an SPRI technique. However, we did not use magnetic beads for isolation during the rinsing steps as in prior methods. Instead, a PC microchannel containing microposts was used as an immobilization bed. Exposing the PC surface to UV light induced a photo-oxidation reaction that produced surface carboxylate groups. We have also quantified the amount of DNA captured in photoactivated PC microchannels, to determine the efficiency of capture and release by this method. Quantitative results were obtained using radio-labeled DNA and scintillation counting. We have also used PC microchannels in SPRI to purify dye-terminator sequencing fragments. DNA was precipitated onto the surface of the PC microchannels, washed, and released in water. The purified sequencing fragments were then loaded into the slab gel of an automated DNA sequencer. We have shown that the PC microchannel could be subjected to multiple purification steps, i.e., it was reusable. We also demonstrated that the PC microchannels used for SPRI could be directly coupled to a capillary gel column for separation.

EXAMPLE 6

Solid-Phase Reversible Immobilization of DNA Sequencing Fragments onto a PC Sheet A PC sheet (25 mm×25 mm×1.0 mm) (Goodfellow, Berwyn, Pa.) was exposed to UV light (254 nm, 0.5 mW/cm$^2$) for 30 min through a photomask. The PC sheet was then washed with isopropanol. The activated PC sheet was then incubated for 10 min with a dye-terminator DNA sequencing fragment mix, which comprised 10 μL of DNA fragments (ranging in size from about 20 bp to about 1000 bp), 10 μL of binding buffer (CleanSEQ, Agencourt, Mass.), and 129 mL of 73% EtOH. The PC sheet was then washed with 73% EtOH. The surface of the PC was subsequently imaged with a near-IR fluorescence scanner. In this system, it was observed that larger DNA fragments had a higher affinity for the surface than the smaller fragments. In addition, the dye-labeled dideoxynucleotides had no affinity for this surface.

EXAMPLE 7

Immobilization of Radiolabelled DNA onto PC Sheet

An oligonucleotide (100 bp) was radiolabelled at the 5' terminus with [γ-$^{32}$P]ATP (Promega, Madison, Wis.). The reaction cocktail comprised 200 pmol DNA, 5 μL of 10× Kinase buffer, 15 μL of [γ-$^{32}$P] ATP (3,000 Ci/mmol), 2 μL of T4polynucleotide Kinase (10 U/μL), and 15 μL of ddH$_2$O. The reaction mixture was incubated at 37° C. for 10 min. The action of the enzyme was halted by adding 2 μL 0.5 M EDTA. Unincorporated dATP was removed with a MicroSpin™ G-25 column (Amersham Pharmacia Biotech, Piscataway, N.J.). The efficiency of $^{32}$P labeling was determined in an assay using a DNA binding filter. The $^{32}$P-labeled DNA (1.0 μL) was spotted onto a circular filter. The filter was dried under a heat lamp, and washed twice with 0.5 M sodium phosphate to remove unincorporated nucleotides. A 0.5 cm$^2$ PC sheet was activated by UV irradiation (without a mask), and incubated with $^{32}$P-labeled DNA as described above. Radioactivity was measured by submerging the sample into a vial containing a scintillation cocktail, and monitoring the radioactivity using an LS6000IC™ series scintillation counter (Beckman Instruments, Fullerton, Calif.).

EXAMPLE 8

We measured the amount of DNA that was captured by this technique, using $^{32}$P-labeled DNA. The amount of radioactivity generated from the PC sheet, activated and incubated as described above, was measured by submerging the entire sheet into a vial containing a scintillation cocktail and monitoring the activity with a scintillation counter.

TABLE 5.1

Measurements of DNA immobilized on the activated PC surface.

| | |
|---|---|
| PC surface area | 0.5 cm$^2$ |
| Specific activity of DNA | 55696 cpm/pmol |
| Scintillation intensity | 128968 cpm |
| Moles of immobilized DNA | 3.9 pmol/cm$^2$ |

EXAMPLES 9-10

PC Microchannel Purification of DNA Fragments for Slab Gel

Dye-terminator sequencing fragments were purified for slab gel electrophoresis within a mechanically-milled, 30 μL PC channel. This relatively large volume allowed for the facile manipulation of the sequencing mix for manual gel loading. Four channels were used, one for each terminator. Each channel was filled with an appropriate purification mix, comprising 10 μL of ddATP, ddCTP, ddGTP or ddTTP sequencing fragments; 10 mL of binding buffer (CleanSEQ™, Agencourt, Beverly, Mass.), and 129 μL of 73% EtOH. The channel was washed twice with 73% EtOH, and was then air-dried for 10 min and subsequently filled with ddH$_2$O (10 min). The eluate was transferred into a centrifuge tube and concentrated to ~1.5 μL in an Eppendorf Concentrator (Brinkman Instruments Inc., Westbury, N.Y.), and then mixed with 1 μL of loading dye.

Sequencing was performed on a LI-COR model 4000 automated DNA sequencer (LI-COR, Lincoln, Nebr.). The sieving matrix was an 8% cross-linked polyacrylamide gel (FMC Bioproducts Long Ranger, Rockland, Me.) that contained 7.0 M urea as the denaturant and 1×TBE (pH 8.0). Polymerization of 30 mL of the 8% gel was initiated by adding 200 μL of 10% (w/v) ammonium persulfate and 20 μL TEMED. A 1.2 μL volume of each sample was loaded into the sample wells, and the samples were electrophoresed at 1,650 V for 8 hours. Data acquisition and base-calling were performed using LI-COR software.

Single base tracks purified in each of four channels were loaded into separate lanes of the sequencer. Using the base caller for the Li-COR 4000 automated DNA sequencer, we were able to read 620 bases from a slab gel electropherogram, with 7 ambiguous bases (calling accuracy ≈99%).

In a similar manner, we used commercial magnetic beads to purify dye-terminator products for sequencing. In this case, we were able to read 629 bases with 8 ambiguous bases. In other words, the PC channels allowed the generation of high-quality sequencing data by effectively removing the excess dye-terminators, with results comparable to those obtained with a more conventional magnetic bead cleanup. As compared to traditional ethanol precipitation protocols (data not shown), the novel SPRI method increased the read length by about 20 bases.

To investigate the reusability of the PC purification channel, a channel was subjected to 4 rounds of SPRI purifications, with each round analyzed on the LI-COR DNA sequencer. For these experiments, G or C terminator tracts were analyzed. G and C tracks for one test sample appeared to be identical after four purification runs, with copious ddH$_2$O washings between rounds to remove any DNA fragments potentially remaining from a previous round. To rule out the possibility that any fragments were retained between rounds, G and C fragments were alternated in the same channel, with the results clearly showing that the previous fragments had been washed out, and that any sample carryover between rounds was negligible. We found that we could reuse the activated PC surface over 12 times, without significant loss in capture efficiency of DNA sequencing fragments.

EXAMPLE 11

PC Microchannel Purification of DNA Fragments for Capillary Gel

Figure 5:
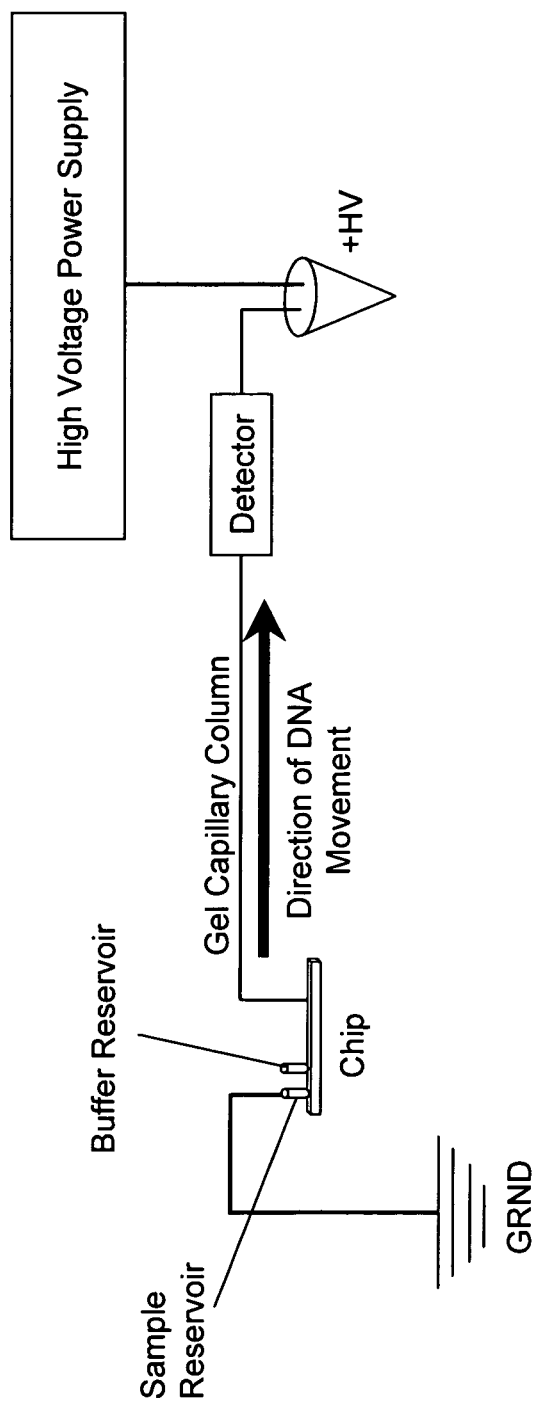
FIG. 5 depicts a schematic diagram of an instrument set-up for integrating a PC-SPRI microchannel with capillary gel electrophoresis

FIG. 5 depicts a schematic diagram of the instrument setup for integrating the PC-SPRI microchannel with capillary gel electrophoresis. The inner diameter of the separation column was 75 μm, with a total length of 75 cm, 50 cm to the detection window. The microchannel was 500 μm wide, 50 μm deep, and 5.5 mm long. The gel column was connected to the microchannel through a sample reservoir in the microchip. The separation matrix was POP 6™ (Applied Biosystems, Foster, Calif.), with 7 M urea as the denaturant. The DNA fragments were detected with a custom-built, near-IR laser-induced fluorescence system. These reservoirs were formed from 500 μm i.d. holes drilled through the 5 mm chip thickness. The microchannel was filled with the purification mix using a micro-syringe through the sample input reservoir. The purification mix comprised 10 μL of ddGTP sequencing fragments, 10 μL of binding buffer (CleanSEQ™, Agencourt, Beverly, Mass.), and 129 μL of 73% EtOH. After incubation for 10 min, the microchannel was washed twice with 73% EtOH. The microchannel was then evacuated and filled with ddH$_2$O.

Following purification, the gel-filled separation column was attached directly to the microchannel through the outlet sample reservoir. As the sequencing fragments eluted from the microchannel, they were electrokinetically injected into the gel column for separation by applying +15 KV at the anodic end of the gel column for 45 s, with the cathodic end of the microchannel grounded. Following injection, the gel column was disconnected from the microchannel and inserted into a cathodic reservoir filled with running buffer for separation. The field strength was set to 200 V/cm during electrophoresis. The running buffer was a 3700 buffer with EDTA (Applied Biosystems, Foster, Calif.).

EXAMPLES 12 and 13

Chip Fabrication

Figure 4:
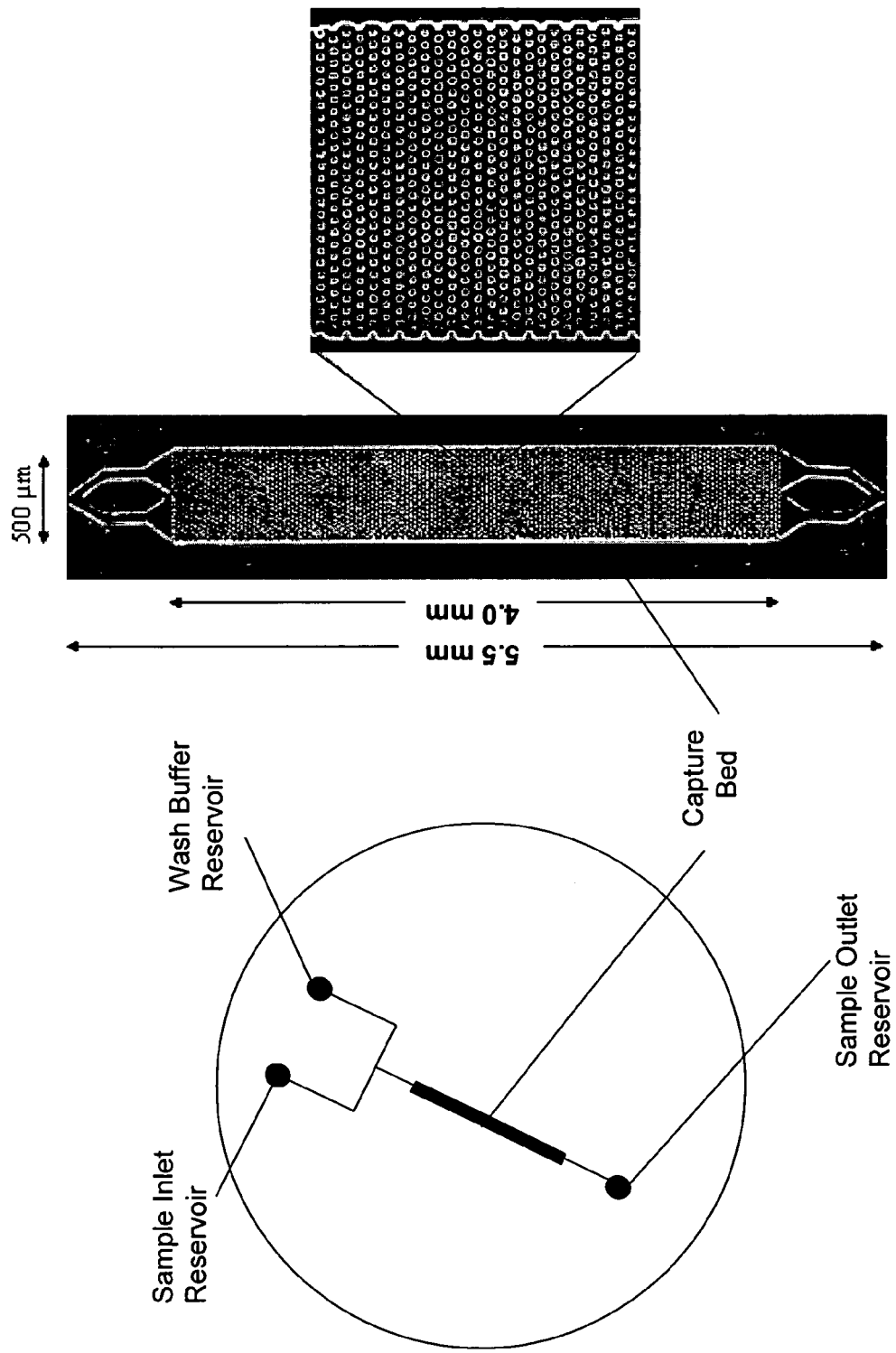
FIG. 4 depicts an optical micrograph of an SPRI capture bed, embossed in PC from a metal die.

Microchips for SPRI were connected to the capillary gel electrophoresis column and were fabricated in PC using LIGA procedures. Briefly, a metal molding die was first fabricated, comprising raised Ni microstructures electroplated onto a stainless steel base plate. FIG. 4 is an optical micrograph of this SPRI capture bed, embossed in PC from the metal die. The microchannel bed was filled with an ordered array of microposts (d=10 μm; spacing=10 μm), to increase the surface area available for loading large amounts of DNA.

Replicates of the molding die were hot embossed into PC. The embossing system comprised a PHI Precision Press™ model TS-21-H-C (4A)-5 (City of Industry, Calif.). A vacuum chamber was installed in this press (pressure <0.1 bar) to enhance complete filling of the die. The wafers inserted into the press were 133 mm in diameter, and the maximum area that could be patterned was 100 mm×100 mm. Before molding, residual water in the polymer was removed by baking the PC wafers in an oven at 80° C. for 8 hours. The die was coated with a release agent, MoldWiz™ (Axel, Woodside, N.Y.), to improve demolding. During embossing, the molding die was heated to 180° C. and pressed into the PC wafer with a force of 1000 lbs for 4 min. While the pressure was being applied, the temperature of the die was increased to 185° C. After 4 min, the press was opened and the polymer part removed and cooled. The PC wafer was maintained at 85° C. throughout the demolding process. The molded parts were exposed to UV light as described above, and the final devices were assembled by annealing two devices together at 154° C. in a circulating air oven for 20 min. Each microchannel possessed $2.1 \times 10^7$ $\mu m^2$ total available surface area, and $1.6 \times 10^8$ $\mu m^3$ net volume.

EXAMPLE 14

SPRI and Capillary Gel Electrophoresis

SPRI has been used to isolate PCR products in the presence of polyethylene glycol (PEG) and NaCl. Unfortunately, high NaCl concentrations are known to inhibit the electrokinetic injection of DNAs in capillary gel electrophoresis, which can result in a significant variation in peak height. In addition, PEG contamination tends to reduce the sequencing trace quality, and generally requires several washes prior to gel loading. Seventy percent ethanol is commonly used to desalt and precipitate DNA. However, excess dye terminators from the sequencing reactions will also bind to the carboxylated solid surface when this buffer is used. DNA precipitation can be induced through changes in the dielectric constant of the solution. Tetraethylene glycol (TEG) has desirable properties as an additive, which include its low dielectric constant, high polarity, low viscosity, neutral charge, and a density greater than that of water. Binding buffers for magnetic bead purification of DNA fragments often incorporate TEG and ethanol.

In the work reported here, we adopted a buffer comprising a combination of 57.4% ethanol and 5% TEG for selective binding of the sequencing fragments prior to capillary gel electrophoresis.

Water has been reported to give better peak resolution from electrokinetic injection into capillaries than typical formamide/EDTA solutions. The presence of other ionic species can significantly decrease the amount of DNA loaded onto a capillary column. Since the ion concentration is low in ddH$_2$O, DNA is preferentially loaded during electrokinetic injection. The use of high loading and thin injection plugs can improve both read length and resolution. To improve data quality, we used ddH$_2$O to elute DNA fragments from the PC microchannel.

In SPRI, the efficiency of DNA binding to the solid surface is a function of the DNA size, with shorter DNA fragments having lower binding efficiencies. This characteristic is of benefit in capillary gel electrophoresis DNA sequencing, since the amount of sample injected into the column depends on the field strength, time of injection, and mobility of the sample in the column matrix. DNA fragments migrate through the gel matrix at a rate dependent on the size of the fragments. It is therefore common to observe biasing effects, in which shorter DNAs are loaded more effectively than longer DNAs. One therefore typically observes smaller fluorescence signals for larger DNAs. Due to the low binding efficiency of short DNA fragments in SPRI, the biasing effect induced by electrokinetic injection is counteracted by SPRI, producing a more uniform peak height in the sequencing trace.

Figure 6:
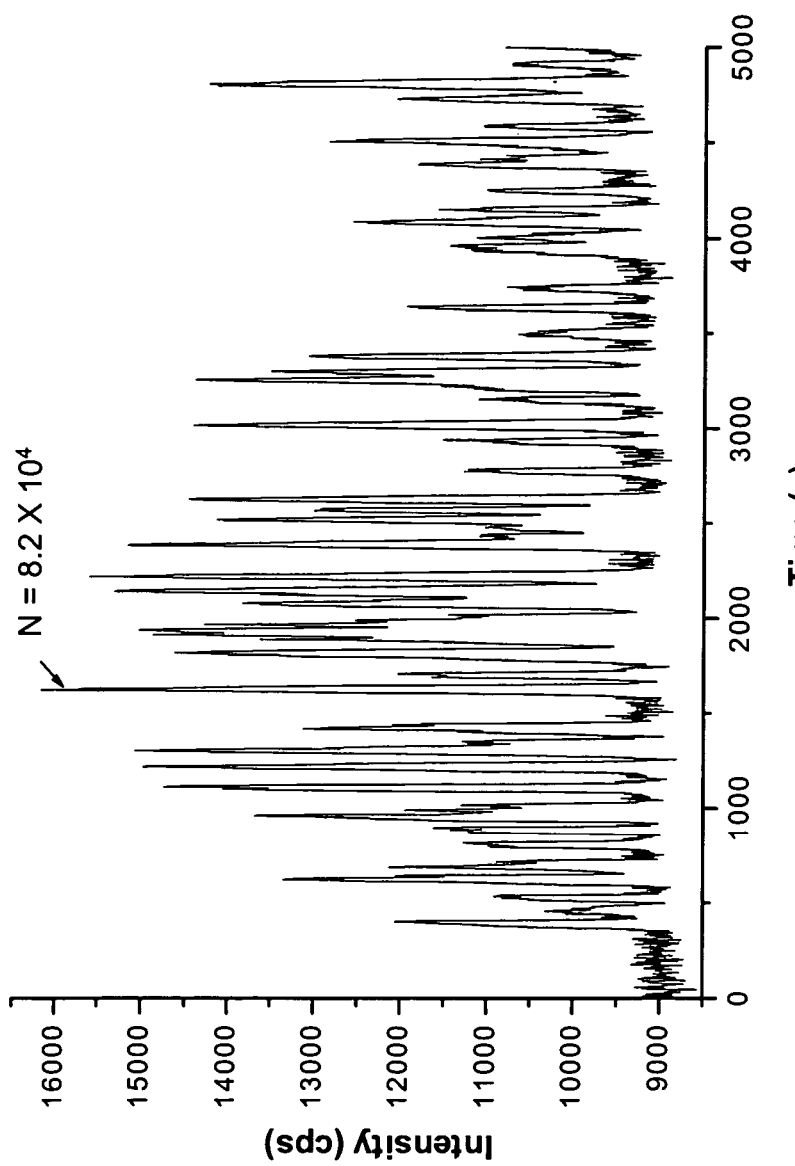
FIG. 6 depicts a capillary electropherogram for near-IR dye A-terminated fragments purified in a PC microchannel, with subsequent separation by capillary gel electrophoresis.

Integration of the novel PC microchannels to capillary gel electrophoresis was studied using the PC microchannel described above with microposts to increase the amount of DNA captured as compared to an open channel. FIG. 6 depicts a capillary electropherogram for near-IR dye A-terminated fragments purified in the PC microchannel, with subsequent separation by capillary gel electrophoresis. The fluorescence of the labeling dye was excited with 5 mW of laser power at 780 nm. The column length, from injector to detector, was 50 cm, with a total length of 75 cm. The separation matrix was POP 6 gel. Electrophoresis was conducted at a field strength of 200 V/cm. Prerun was conducted for 2400 s. FIG. 6 shows 5000 s of data.

The data clearly indicated that excess dye-terminators had been eliminated. The increase in the surface area-to-volume ratio in the microchannels with microposts increased the available immobilization sites. A significant advantage was that DNA fragments eluted from the microchannels could be directly injected into the gel column for separation, eliminating the need for pre-concentration. The electropherogram shown in FIG. 6 would allow an estimated effective read length of ~450 bases, a value that was determined by peak counting in the electropherogram where resolution permitted single-base identification (R>0.7), and then multiplying by 4 (because only A-terminated fragments are shown in FIG. 6.)

We thus successfully demonstrated the use of the novel PC-SPRI format for the purification of dye terminator DNA sequencing fragments, and the integration of this process with both slab and capillary gel electrophoresis. The method has been demonstrated to produce high quality sequencing results using dye-terminator chemistry. The protocol is easy and rapid to conduct, requiring no special treatment of the sequencing reagents, primers, or templates. The microchannel may be scaled to ultra-small volumes, allowing a significant reduction in expensive consumables. Another attractive feature of this microchannel format is the ability to perform multiple purifications from a single chamber. By contrast to more traditional ethanol precipitation methods, the novel method requires no centrifugation, and is conducive to automation. In addition, the PC microchannel can be integrated to high-speed capillary gel electrophoresis. Moreover, the cleanup protocol can be integrated in a single microchip format. The sequencing products purified in PC-SPRI microchannels may be electrokinetically loaded onto a microfabricated multichannel device to perform high speed electrophoretic sorting of DNA fragments.

EXAMPLE 15

Formation of Sensing Probe Patterns on Modified PMMA Planar Waveguides

Waveguides have been used as an excitation medium in fluorescence-based immunosensing for over 25 years. Several evanescent-wave-based fluorometric heterogeneous immunoassays have been developed, particularly some based on optical fibers. In recent years, both planar total-internal reflection elements and planar waveguides have been used as the excitation medium; several methods exist for patterning such planar substrates with antibodies or antigens. Furthermore, planar waveguide substrates that have been patterned with antibodies may be integrated into microfluidic devices so that multiple analytes can be investigated at once in a single sample (i.e, there is no need for separation before detection) The integration of multiple-analyte immunoassays with microfluidic devices makes possible the development of a myriad of portable immunoassays with applications in fields ranging from cancer detection to environmental monitoring.

Two important factors have led to the successful demonstration of microfluidic multiple-analyte immunoassays (MMAIAs): (1) the availability of waveguides that are capable of being chemically modified for immobilizing proteins (e.g., antibodies or antigens), while retaining the capability to propagate homogeneous evanescent wave fields over relatively small dimensions (i.e., an electric field that extends beyond the wave guide to allow excitation in a solution layer adjacent to the wave guide); and (2) the availability of multiple sensing probes lacking cross-reactivity for one another's respective analytes, allowing the simultaneous detection of multiple analytes in a single sample.

Typical waveguide materials for MMAIAs include, e.g., silica glass and silicon oxynitride. A principal criterion is that the refractive index of the waveguide should be greater than that of the medium with which it is in contact. In addition, the waveguide should be of a suitable thickness to support a high number of reflections per unit length of the waveguide. Satisfying these conditions allows the production of a uniform evanescent wave field along the waveguide, so that the attached molecules are excited in a spatially uniform way. Such properties have distinct advantages when using patterned arrays of antibodies with small dimensions. Polymer-based waveguides have been of great interest recently for use in telecommunication devices and miniaturized systems. Recently, LIGA-based methods have been used to form waveguides from PMMA. For example, single- and multi-mode waveguides made of PMMA have been constructed and operated effectively over a wide spectral region (e.g., 400-1700 nm). LIGA-based and similar molding techniques can be used to form PMMA-based waveguides.

Figure 7:
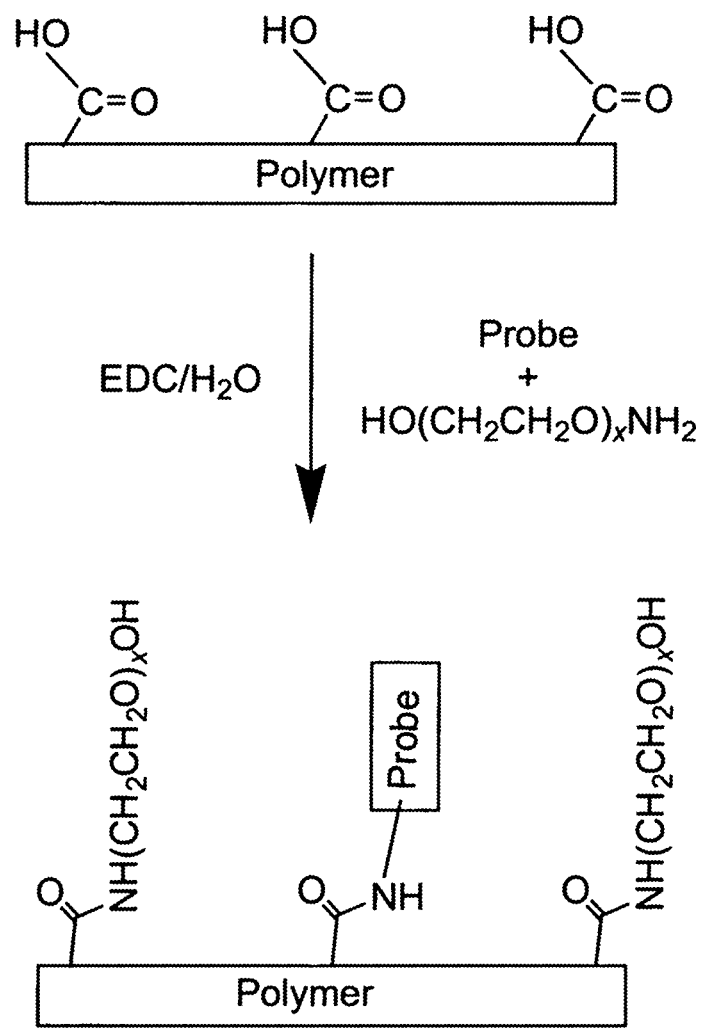
FIG. 7 depicts a reaction scheme for immobilization of sensing probes (recognition elements) on a modified polymer surface.

See FIG. 7 for a schematic depiction of one embodiment employing this aspect of the present invention. Sensing probes are linked to a polymeric surface that has been patterned with carboxylate groups, e.g., by exposure of a PMMA surface to UV light through a photomask. The sensing probes are then attached to the carboxylic acid patterns, for example, by aqueous-phase carbodiimide coupling strategies using 1-ethyl-3-(3-dimethylaminopropyl)carbodiimide, EDC, and amine groups on the antibodies, or "molecular beacon" nucleic acid hybridization probes. To better distribute the sensing probe molecules homogeneously on the modified PMMA surface (on the assumption that well-separated probes will react better with solution-phase targets), the amine-labeled probes are conjugated to the carboxylic acid surface in the presence of an ethylene glycol amine, $HO(CH_2CH_2O)_xNH_2$. The ratio of glycol amine to sensing probe may be varied; after fluorescence labeling/activation of the surface probes (e.g., by adding complementary oligonucleotides to the molecular beacon nucleic acid surfaces, or adding fluorescently tagged antibody that is specific to the immobilized antibody bound to the surface), the surface is interrogated by evanescent fluorescence laser microscopy. The results of these experiments are used to determine appropriate sensing probe:ethylene glycol amine ratios in the immobilization step. In addition, the immobilized ethylene glycol groups inhibit non-specific adsorption of other nucleic acids and/or proteins.

Patterns of the various sensing probes designed for a particular study are formed sequentially in the microchannel/wave guide regions. For example, if an antibody and three molecular beacon oligonucleotides are to be immobilized in a given channel/wave guide region, then the patterning of the polymer is preferably conducted so as to provide only one "spot" of carboxylates that can be derivatized with the chosen sensing probe, using the immobilization protocol outlined in FIG. 7. Subsequent exposures and immobilizations may thereafter be conducted for each sensing probe.

To inhibit "labeling" of carboxylate sites on the previously immobilized protein sensing probes (e.g., antibodies), the carboxylate groups of the immobilized proteins may be blocked, for example by capping with amines using aqueous carbodiimide coupling methods. Then, amine-terminated oligonucleotides can be attached to newly carboxylated patterns using the sequential photo-patterning method, with minimal attachment to the previously immobilized proteins.

EXAMPLE 16

Formation of DNA Microarrays by Photopatterning

DNA microarrays may be configured with the novel method to detect sequence variations at many different sites simultaneously, a technique that is useful, for example, in diagnostic applications. Such arrays typically comprise thousands of short oligonucleotide probes (e.g., ~20 mers) having known sequences. In prior techniques for preparing DNA microarrays, the oligonucleotides are typically attached covalently or non-covalently to a two-dimensional solid surface, for example to glass via siloxane chemistry, or to poly-lysine coated slides electrostatically. Some of the limitations associated with prior DNA microarrays include the extended hybridization times required to generate an optimal response (diffusion-controlled passive hybridization), the instability of the linkage chemistries (which are hydrolytically unstable), and the large quantity of sample that is typically required to interrogate the array.

The novel technique may be used to make arrays in polymer-based microfluidic chips to detect particular nucleotide sequences, for example, in the detection of low-frequency mutations. A preferred material in making such microfluidic devices is poly(methyl methacrylate), PMMA. (PC is not preferred for applications where its autofluorescence might interference with fluorescence measurements of target species.)

Further advantages may result from merging microarray technology with microfluidic platforms, as others have done using different techniques, advantages that include the reduced quantity of sample required to address each element of the array, enhanced mass transport to the array surface, reduced analysis time, the ability to monitor several samples simultaneously using multi-channel chips, and a reduced potential for contamination resulting from the closed architecture of the microfluidic channel.

In prototype experiments, a PCR/LDR assay is carried out on K-ras genes to detect point mutations with clinical relevance in diagnosing colorectal cancers. Using pre-synthesized oligonucleotides, an array containing the appropriate "zip codes" is micro-printed into microfluidic channels hot-embossed in PMMA. The array spots could be patterned into the floor of the device using the photoactivation procedures discussed above. A photomask is used to produce surface carboxylate groups, which serve as an anchoring site for amine-terminated oligonucleotides via an amide bond formed by EDC coupling chemistry, and the array is accessed using microfluidics. The surface chemistry and microfluidic chip are optimized to increase the loading level of the oligonucleotide probes, to improve the stability of the linkage chemistry, to facilitate repeated use of the array, to increase the kinetic rate of hybridization in the microfluidic channel, and to demonstrate high sensitivity for this hybridization assay (detection of small numbers of mutant DNA in a background of a substantially larger number of wild-type DNAs). See. e.g., Y. Wang et al., "Microarrays assembled in microfluidic chips fabricated from poly(methyl methacrylate) for the detection of low-abundant DNA mutations," *Anal. Chem.*, vol. 75, pp. 1130-1140 (2003), which employed a generally similar approach, except that mechanical and chemical means were used to spot oligonucleotide probes onto a PMMA surface.

EXAMPLE 17

UV Activation of PMMA Surface for Oligonucleotide Probe Attachment

PMMA sheets (20 mm×20 mm×1.0 mm) (Goodfellow, Berwyn, Pa.) were cut, the manufacturer's protective films were removed, and the surfaces were rinsed with isopropanol and ddH$_2$O. On some of the slides, a central spot, 0.5 cm diameter, was exposed to broadband UV light (15 mW/cm$^2$) for 30 min, while other slides were left unexposed. The slides were then rinsed again with isopropanol and ddH$_2$O, and were dried with compressed air. A 5'-terminal C$_6$-amino-modified oligonucleotide was dissolved in 0.5 M EDC, 100 mM MES buffer (pH 6.4), to prepare a 10 μM oligonucleotide solution. Then, 20 μL of the prepared oligonucleotide solution was spotted onto the centers of both a UV-treated PMMA slide, and of an otherwise identical PMMA slide that had not been exposed to UV light. The slides were incubated at 37° C. overnight. The slides were then washed with ddH$_2$O, and dried. They were then hybridized in 10 nM M13 IRD 800 dye-labeled complementary sequence oligonucleotide solution (in 5×SSPE, 0.1% SDS) at 60° C. for one hour. The hybridized slides were then washed twice (15 min per wash) with 2×SSPE and 0.1% SDS. Under an infrared scanner, the untreated slide showed no hybridization signal, while the treated slide showed a strong fluorescence signal in the area of the treated spot—having a signal about 10 times stronger than the background signal from the untreated PMMA.

EXAMPLES 18-20

Figure 8:
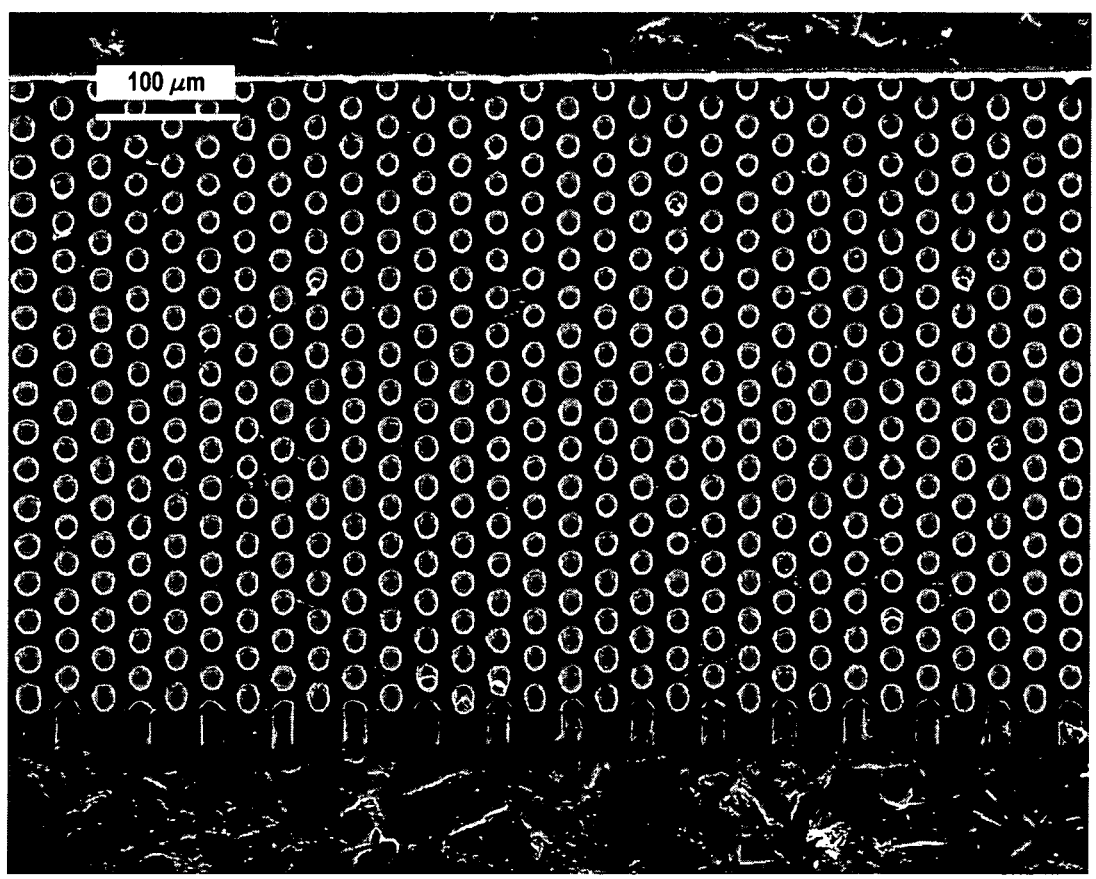
FIG. 8 depicts a photomicrograph of a microfluidic chip fabricated in PMMA that contains microposts.
Figure 9A:
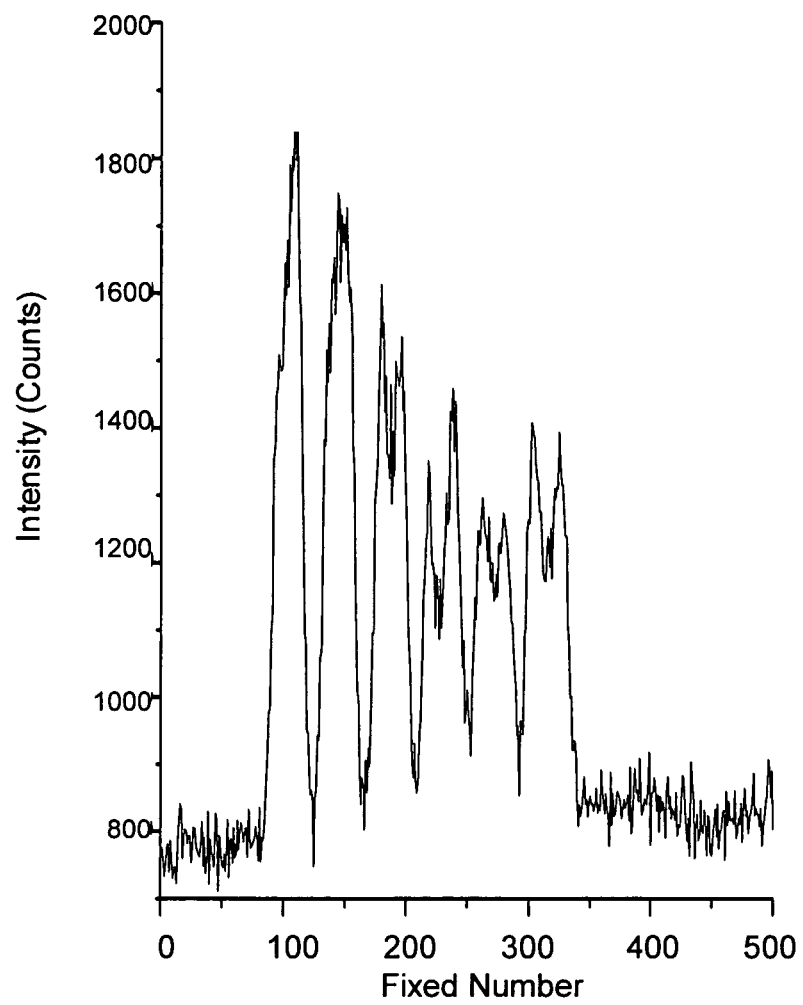
FIGS. 9(a) and 9(b) depict hybridization signals from assays carried out in a microchannel with an "open" footprint, and one having microposts within it, respectively.
Figure 9B:
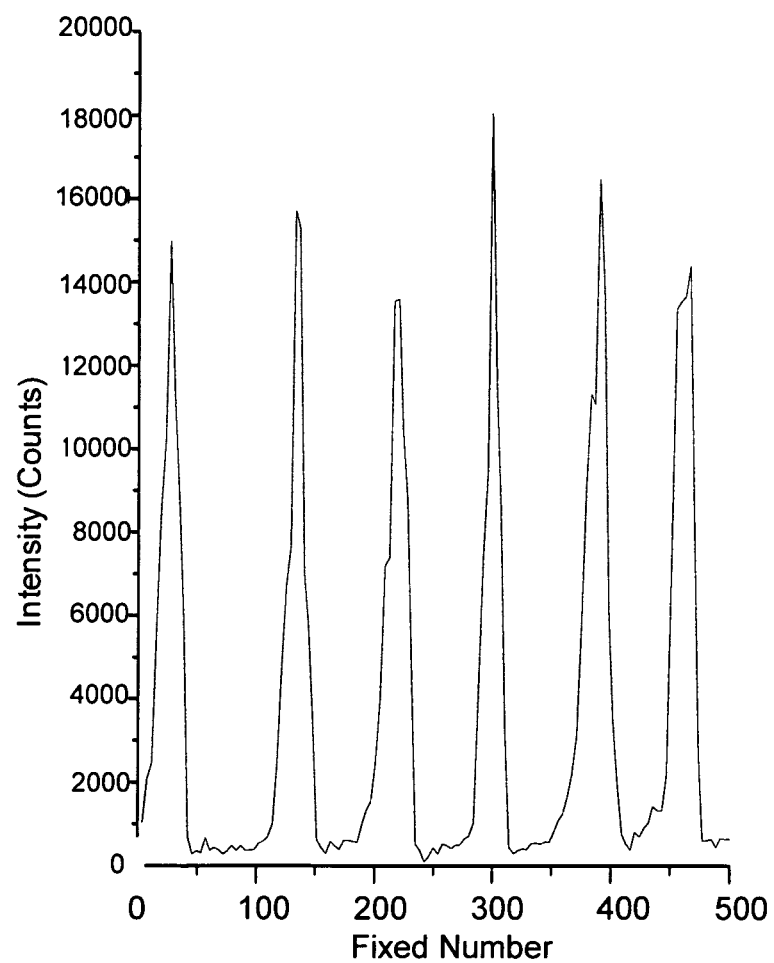

The available "signal" for DNA microarrays may be increased by forming three-dimensional microstructures in microfluidic chips. FIG. 8 is a photomicrograph of a microfluidic chip fabricated in PMMA that contains microposts. Each micropost was 10 μm in diameter, with a center-to-center spacing of 20 μm. Such channels with increased surface area were Photoactivated with UV light, and oligonucleotide probes were then spotted onto the activated surface. FIGS. 9(a) and 9(b) depict the hybridization signals from assays that were carried out in a microchannel with an "open" footprint, and one having microposts within it, respectively. The PMMA surface was exposed to UV light for 10 min, and then the arrays were assembled by spotting 34-base pair, amine-terminated probes to the activated surface through an amide bond via EDC coupling. The chip was then flooded with fluorescent-labeled oligonucleotide complements (1.0 nM), washed, and imaged with a laser confocal fluorescence imager. The signal intensity was about ten times stronger in the channel with microposts as compared to the signal from the open channel.

Definition. As used in the specification and Claims, unless context clearly indicates otherwise, a "photoresist" or a "resist" is a compound or composition that acts as a positive or negative resist in response to the wavelength(s) of actinic light used, at the fluence used, in a particular process to generate or create a pattern on another material, i.e., the polymer substrate. Any photoresist in areas not corresponding to the pattern is typically removed from the substrate during development, after creation of the pattern. Likewise, a photoresist or resist is considered to be absent under this definition if any component that acts as a resist in response to the actinic light that is used in a particular process is present only in insubstantial amounts, or is absent completely. By way of example, the following could be considered photoresists under this definition, if the actinic light to which each is responsive were present in the particular process: visible light resists, near ultraviolet resists, ultraviolet resists, and far ultraviolet resists. Note that this definition refers to the actinic light that is used in a particular process. Thus, for example, even though PMMA is a well-known photoresist with respect to X-ray radiation, PMMA does not ordinarily act as a photoresist with respect to ultraviolet light. For example, under the conditions described here, PMMA does not act as a UV photoresist. Thus, within the scope of this definition, in a particular process in which ultraviolet light is used, but in which no substantial amount of X-ray radiation is present, PMMA would not be considered to be a "photoresist." Note also that this definition refers to the fluence used in a particular process. A compound that does not act as a photoresist in response to the fluence of actinic light used in a particular process, but that might act as a photoresist in response to a higher fluence of light at the same wavelength, is nevertheless not considered to be a photoresist within the scope of this definition. The novel technique does not require the use of a photoresist; rather, the polymer itself acts directly as the photoactive substrate.

A polymer (or polymer surface) is considered to be "essentially free" of any photoresist if the polymer (or surface) contains no photoresist, as defined above. A polymer (or polymer surface) is also considered to be "essentially free" of any photoresist where the polymer (or surface) contains small amounts of a photoresist, but where the concentration of any such photoresist that is present is sufficiently small that the response of the polymer (or surface) to the light employed, at the fluence used in the exposed portion of the surface, is substantially the same as would be the response of a hypothetical polymer (or surface) that was otherwise identical, but that contained no photoresist.

Miscellaneous. The complete disclosures of all references cited in the specification are hereby incorporated by reference. Also incorporated by reference are the following works of the inventors, none of which are prior art to this application: B. Vaidya et al., "Micro-patterning and metal deposition on polymer surfaces," abstract, 223rd ACS National Meeting (Apr. 7-11, 2002); B. Vaidya et al., "Photoresist-free micropatterning of polymer surfaces used in microanalytical devices," presentation, Micro Total Analysis Systems (November 2002); and Y. Xu et al., "Solid-Phase Reversible Immobilization in Microfludic Chips for the Purification of Dye-Labeled DNA Sequencing Fragments," *Anal Chem.*, vol. 75, pp. 2975-2984 (2003). In the event of an otherwise irreconcilable conflict, however, the present specification shall control.

While most of the examples given above employed ultraviolet light, those of skill in the art will recognize that actinic light of other wavelengths may be used in practicing this invention as well, including both deep ultraviolet and visible light. Wavelengths longer than X-rays should be used, however. More generally, the wavelength of the actinic light should be longer than about 190 nm.

We claim:
1. A process comprising the steps of:
(a) selectively exposing a polymer substrate in an oxidizing atmosphere to actinic light, wherein:
(i) the polymer substrate comprises a polymeric or copolymeric composition containing one or more functionalities that will undergo photooxidation to produce carboxyl groups that remain bound to the polymer surface, when the polymer surface is exposed to actinic light in an oxidizing atmosphere; wherein said photooxidation comprises the surface oxidation of one or more of said functionalities by oxygen or other oxidizing agent in the oxidizing atmosphere;
(ii) the light selectively exposes portions of the polymer surface in accordance with a pre-determined pattern, while not exposing the remaining portions of the polymer surface to substantial light;
(iii) the fluence of light in the exposed portions of the polymer surface suffices to induce photooxidation of polymer on or near the polymer surface by the reaction of one or more of said functionalities with oxygen or other oxidizing agent in the oxidizing atmosphere, sufficient to generate substantial quantities of carboxyl groups that remain bound to the polymer surface, but insufficient to cause substantial photoablation of polymer surface in the exposed portions;
(iv) the fluence of light in the unexposed portions of the polymer surface is zero, or is insufficient to induce the generation of substantial quantities of carboxyl groups that remain bound to the polymer surface;
(v) the polymer surface is essentially free of any photoresist that is responsive to the actinic light at the fluence applied to the exposed portions of the polymer surface;
(vi) the polymer substrate is not a polyimide; and
(b) reacting the resulting, bound carboxyl groups with one or more reactants, to impart chemical functionality to the exposed portions of the polymer surface different from carboxyl functionality, while not imparting substantial amounts of the same type of chemical functionality to the unexposed portions of the polymer surface; wherein:
(vii) the one or more reactants are selected from the group consisting of amines, imides, azides, azo compounds, cyanates, thiols, anhydrides, thionyl halides, metal oxides, ceramics, piezoelectric materials, semiconductors, oligonucleotides, antibodies, antigen-binding portions of antibodies, antigens, enzymes, non-enzymatic peptides, non-enzymatic proteins, polymers, reduced metals, and oxidized metals;
(viii) the one or more reactants comprise a chemical group with which the bound carboxyl groups react; wherein the chemical group is selected from the group consisting of amines, imides, azides, azo compounds, cyanates, thiols, anhydrides, thionyl halides, metal oxides, oligonucleotides, antibodies, antigen-binding portions of antibodies, antigens, enzymes, non-enzymatic peptides, non-enzymatic proteins, reduced metals, and oxidized metals; and
(ix) provided that, if the reactant is an amine, then said process additionally comprises the step of reacting the amine with carboxyl bound to the polymer to produce an amide group that is covalently linked to the polymer.

2. A process as recited in claim 1, wherein the actinic light comprises ultraviolet light, deep ultraviolet light, or near ultraviolet light.

3. A process as recited in claim 1, wherein the actinic light comprises visible light.

4. A process as recited in claim 1; wherein the fluence of light on the exposed portions of the polymer surface suffices to generate at least about $10^{-12}$ moles per $cm^2$ of carboxyl groups that remain bound to the polymer surface; wherein the fluence of light on the exposed portions of the polymer surface is insufficient to cause photoablation of polymer deeper than about 250 nm; and wherein the fluence of light on the unexposed portions of the polymer surface is zero, or is sufficient to induce the generation of not more than about $5 \times 10^{-13}$ moles per $cm^2$ of carboxyl groups that remain bound to the polymer surface.

5. A process as recited in claim 1, wherein the one or more reactants are selected from the group consisting of oligonucleotides, antibodies, antigen-binding portions of antibodies, antigens, enzymes, non-enzymatic peptides, and non-enzymatic proteins.

6. A process as recited in claim 1, wherein the one or more reactants comprise a reduced or oxidized metal; or wherein said process additionally comprises the step of reacting the chemical functionality with a reduced or oxidized metal to bind the metal to the functionality.

7. A process as recited in claim 6, wherein the reduced or oxidized metal is selected from the group consisting of copper, nickel, gold, silver, platinum, and palladium.

8. A process as recited in claim 1, wherein the chemical functionality comprises at least one nitrogen, oxygen, or sulfur atom having a lone pair of electrons; and wherein said process additionally comprises the step of coordinating at least one reduced or oxidized metal atom to the nitrogen, oxygen, or sulfur atom's lone pair of electrons.

9. A process as recited in claim 1, wherein the chemical functionality comprises at least one nitrogen, oxygen, or sulfur atom having a lone pair of electrons; and wherein said process additionally comprises the sequential steps of: (a) coordinating at least one oxidized metal atom to the nitrogen, oxygen, or sulfur atom's lone pair of electrons; and (b) reducing the coordinated metal atom in situ; whereby reduced metal is selectively bound to the exposed portions of the polymer surface.

10. A process as recited in claim 1, wherein the one or more reactants are selected from the group consisting of metal oxides, ceramics, piezoelectric materials, and semiconductors.

11. A process as recited in claim 1, wherein the one or more reactants are selected from the group consisting of amines, imides, azides, azo compounds, cyanates, thiols, anhydrides, and thionyl halides.

12. A process as recited in claim 1, wherein: (a) the one or more reactants comprise a second polymer; or (b) the one or more reactants additionally comprise a polymer initiator or a monomer, and said process additionally comprises the step of forming a second polymer bound to the first polymer in situ by reaction of monomer with the bound initiator or bound monomer.

13. A process as recited in claim 1, additionally comprising the step of binding one or more whole, respiring cells to the chemical functionality on the polymer surface.

14. A process as recited in claim 1, wherein the polymer substrate is selected from the group consisting of acrylate polymers, aromatic polymers, and polycarbonates.

15. A process as recited in claim 1, wherein the polymer substrate comprises a polysulfone.

16. A process as recited in claim 1, wherein the polymer substrate comprises poly(methyl methacrylate).

17. A process comprising the steps of:
(a) selectively exposing a polymer substrate in an oxidizing atmosphere to actinic light, wherein:
  (i) the polymer substrate comprises a polymeric or copolymeric composition containing one or more functionalities that will undergo photooxidation to produce carboxyl groups that remain bound to the polymer surface, when the polymer surface is exposed to actinic light in an oxidizing atmosphere; wherein said photooxidation comprises the surface oxidation of one or more of said functionalities by oxygen or other oxidizing agent in the oxidizing atmosphere;
  (ii) the light selectively exposes portions of the polymer surface in accordance with a pre-determined pattern, while not exposing the remaining portions of the polymer surface to substantial light;
  (iii) the fluence of light in the exposed portions of the polymer surface suffices to induce photooxidation of polymer on or near the polymer surface by the reaction of one or more of said functionalities with oxygen or other oxidizing agent in the oxidizing atmosphere, sufficient to generate substantial quantities of carboxyl groups that remain bound to the polymer surface, but insufficient to cause substantial photoablation of polymer surface in the exposed portions;
  (iv) the fluence of light in the unexposed portions of the polymer surface is zero, or is insufficient to induce the generation of substantial quantities of carboxyl groups that remain bound to the polymer surface;
  (v) the polymer surface is essentially free of any photoresist that is responsive to the actinic light at the fluence applied to the exposed portions of the polymer surface; and
(b) reacting the resulting, bound carboxyl groups with one or more reactants, to impart chemical functionality to the exposed portions of the polymer surface different from carboxyl functionality, while not imparting substantial amounts of the same type of chemical functionality to the unexposed portions of the polymer surface; wherein:
  (vi) the one or more reactants are selected from the group consisting of amines, imides, azides, azo compounds, cyanates, thiols, anhydrides, thionyl halides, piezoelectric materials, semiconductors, oligonucleotides, antibodies, antigen-binding portions of antibodies, antigens, enzymes, non-enzymatic peptides, non-enzymatic proteins, polymers, and reduced metals;
  (vii) the one or more reactants comprise a chemical group with which the bound carboxyl groups react; wherein the chemical group is selected from the group consisting of amines, imides, azides, azo compounds, cyanates, thiols, anhydrides, thionyl halides, oligonucleotides, antibodies, antigen-binding portions of antibodies, antigens, enzymes, non-enzymatic peptides, non-enzymatic proteins, and reduced metals; and
  (viii) provided that, if the reactant is an amine, then said process additionally comprises the step of reacting the amine with carboxyl bound to the polymer to produce an amide group that is covalently linked to the polymer.

18. A process as recited in claim 17, wherein the actinic light comprises ultraviolet light, deep ultraviolet light, or near ultraviolet light.

19. A process as recited in claim 17, wherein the actinic light comprises visible light.

20. A process as recited in claim 17; wherein the fluence of light on the exposed portions of the polymer surface suffices to generate at least about $10^{-12}$ moles per $cm^2$ of carboxyl groups that remain bound to the polymer surface; wherein the fluence of light on the exposed portions of the polymer surface is insufficient to cause photoablation of polymer deeper than about 250 nm; and wherein the fluence of light on the unexposed portions of the polymer surface is zero, or is sufficient to induce the generation of not more than about $5 \times 10^{13}$ moles per $cm^2$ of carboxyl groups that remain bound to the polymer surface.

21. A process as recited in claim 17, wherein the one or more reactants are selected from the group consisting of oligonucleotides, antibodies, antigen-binding portions of antibodies, antigens, enzymes, non-enzymatic peptides, and non-enzymatic proteins.

22. A process as recited in claim 17, wherein the one or more reactants comprise a reduced metal; or wherein said process additionally comprises the step of reacting the chemical functionality with a reduced metal to bind the metal to the functionality.

23. A process as recited in claim 22, wherein the reduced metal is selected from the group consisting of copper, nickel, gold, silver, platinum, and palladium.

24. A process as recited in claim 17, wherein the chemical functionality comprises at least one nitrogen, oxygen, or sulfur atom having a lone pair of electrons; and wherein said process additionally comprises the step of coordinating at least one reduced or oxidized metal atom to the nitrogen, oxygen, or sulfur atom's lone pair of electrons.

25. A process as recited in claim 17, wherein the one or more reactants are selected from the group consisting of piezoelectric materials and semiconductors.

26. A process as recited in claim 17, wherein the one or more reactants are selected from the group consisting of amines, imides, azides, azo compounds, cyanates, thiols, anhydrides, and thionyl halides.

27. A process as recited in claim 17, wherein: (a) the one or more reactants comprise a second polymer; or (b) the one or more reactants additionally comprise a polymer initiator or a monomer, and said process additionally comprises the step of forming a second polymer bound to the first polymer in situ by reaction of monomer with the bound initiator or bound monomer.

28. A process as recited in claim 17, additionally comprising the step of binding one or more whole, respiring cells to the chemical functionality on the polymer surface.

29. A process as recited in claim 17, wherein the polymer substrate is selected from the group consisting of acrylate polymers, aromatic polymers, polyimides, polycarbonates, and polysulfones.

30. A process as recited in claim 17, wherein the polymer substrate comprises a polysulfone.

31. A process as recited in claim 17, wherein the polymer substrate comprises poly(methyl methacrylate).

* * * * *